(12) United States Patent
Kang et al.

(10) Patent No.: US 10,210,589 B2
(45) Date of Patent: Feb. 19, 2019

(54) GENERIC METHOD OF HANDLING DICOM STRUCTURED REPORTING CONTENTS

(75) Inventors: Uan Sharon Kang, Westford, MA (US); Susan Golob, Bedford, MA (US); Sheila Brigid Filteau, Methuen, MA (US)

(73) Assignee: Koninklijke Philips N.V., Eindhoven (NL)

( * ) Notice: Subject to any disclaimer, the term of this patent is extended or adjusted under 35 U.S.C. 154(b) by 1006 days.

(21) Appl. No.: 13/498,342

(22) PCT Filed: Aug. 19, 2010

(86) PCT No.: PCT/IB2010/053758
§ 371 (c)(1),
(2), (4) Date: Mar. 27, 2012

(87) PCT Pub. No.: WO2011/036586
PCT Pub. Date: Mar. 31, 2011

(65) Prior Publication Data
US 2012/0185280 A1    Jul. 19, 2012

Related U.S. Application Data

(60) Provisional application No. 61/246,267, filed on Sep. 28, 2009.

(51) Int. Cl.
| | | |
|---|---|---|
| G06Q 50/24 | (2012.01) | |
| G06F 15/00 | (2006.01) | |
| G16H 30/40 | (2018.01) | |
| G16H 30/00 | (2018.01) | |
| G16H 30/20 | (2018.01) | |
| G16H 10/60 | (2018.01) | |
| G16H 15/00 | (2018.01) | |

(52) U.S. Cl.
CPC .............. *G06Q 50/24* (2013.01); *G16H 10/60* (2018.01); *G16H 15/00* (2018.01); *G16H 30/00* (2018.01); *G16H 30/20* (2018.01); *G16H 30/40* (2018.01)

(58) Field of Classification Search
CPC ............ G06F 19/321; G06F 17/30569; G06F 17/30244; Y10S 707/99945; G16H 30/00; G16H 30/20; G16H 30/40; G06Q 50/24
USPC ........................................................ 705/2–3
See application file for complete search history.

(56) References Cited

U.S. PATENT DOCUMENTS

| | | |
|---|---|---|
| 6,260,021 B1 | 7/2001 | Wong et al. |
| 6,658,483 B1 | 12/2003 | Iwamoto et al. |

(Continued)

FOREIGN PATENT DOCUMENTS

| | | |
|---|---|---|
| CN | 1585948 A | 2/2005 |
| CN | 101052041 A | 10/2007 |

(Continued)

*Primary Examiner* — Joy Chng (57) ABSTRACT

A system and method for mapping standard measurements to local measurements. The system and measurements reading a structured report information object, matching the standard measurements from the structured report information object to corresponding existing local measurements from a local measurement database and generating a summary page including the matched standard measurements and the corresponding existing local measurements and further including unmatched standard measurements that do not correspond to local measurements.

18 Claims, 9 Drawing Sheets

(56) References Cited

U.S. PATENT DOCUMENTS

| | | |
|---|---|---|
| 6,826,578 B2 | 11/2004 | Brackett et al. |
| 2002/0193996 A1 | 12/2002 | Squibbs et al. |
| 2003/0018661 A1 | 1/2003 | Darugar |
| 2007/0008172 A1 | 1/2007 | Hewett et al. |
| 2007/0237371 A1* | 10/2007 | Zhu ..................... G06F 19/321 382/128 |
| 2010/0008553 A1* | 1/2010 | Holmstrom ....... G06F 17/30265 382/128 |

FOREIGN PATENT DOCUMENTS

| | | | | |
|---|---|---|---|---|
| GB | 2376387 A | | 11/2002 | |
| GB | 2376387 A | * | 12/2002 | ........ H04M 1/72544 |
| JP | 08030695 A | | 2/1996 | |
| JP | 2006346973 A | | 12/2006 | |
| WO | 03009517 A2 | | 1/2003 | |
| WO | 03034228 A1 | | 4/2003 | |
| WO | 2004066125 A2 | | 8/2004 | |

\* cited by examiner

| | | | | DICOM Terms (Template 5200 – Adult Echo) [C:\dicom\AdultEchoSR.dcm] | | | | | | Matched Local Measurement Name |
|---|---|---|---|---|---|---|---|---|---|---|
| Site | Target | Target Modifier | Method | Measurement Concept | Imaging Mode | Imaging View | Cardiac Phase | Flow Direction | Respiratory State | |
| Aortic Valve | | | | Deceleration Slope | Doppler Pulsed | | | Retrograde Flow | | AI dec slope |
| Right Ventricle | Right Ventricle Outflow Tract | | | Mean Velocity | | | | Antegrade Flow | | RV V1 mean |
| Left Ventricle | | | Method of Disks, Single Plane | Left Ventricle diastolic major axis | 2D mode | Apical four chamber | End Diastole | | | LVLd ap4 |
| Left Ventricle | | | | Left Ventricle Isovolumic Relaxation Time | | | | | During Expiration | LVIVRT, exp |
| Pulmonary Vein | | Left Lower Segment | | Pulmonary Vein Systolic Peak Velocity | | | | | | LLPuIv S2 max vel |
| Pulmonary Artery | | | | Right Pulmonary Artery Diameter | 2D mode | Subcostal Long Axis | Diastole | | | |

GENERIC METHOD OF HANDLING DICOM STRUCTURED REPORTING CONTENTS

DICOM (Digital Imaging and Communications in Medicine) is an industry standard for transferring medical related information such as images and measurements between medical devices and/or systems via a network or media, by providing a software-based interoperability mechanism. In particular, measurements (e.g., patient information, image data) that are transferred via DICOM protocol are bundled in a software object called a structured report information object (SR Object). The SR Object is transferable through DICOM protocol from an SR Sender (e.g., DICOM medical imaging devices of various modalities such as CT, MR, X-ray, etc.) to SR Receivers (e.g., DICOM PACS systems). The SR Sender sends measurements to the network or writes them to a file on a medium while the SR Receiver receives measurements from the network or reads them from a file on the medium.

Specifically, the SR Sender converts/encodes local measurements to DICOM measurements using DICOM templates and codes. Upon receiving the DICOM measurements, the SR Receiver must convert/decode the DICOM measurements to local measurements according to the DICOM templates and codes. Mapping files are a set of hard-coded files that ship with the medical device/system, which handle mappings between DICOM measurements and local measurements. For the SR Sender, the mapping file determines how to convert the local measurements to DICOM measurements. For the SR Receiver, the mapping file indicates how to convert the DICOM measurement to its local measurement for use by the end-user. The SR Receiver may include a set of mapping files, one mapping file corresponding to each target SR Sender systems from which it may receive DICOM measurements.

This mapping file approach, however, has its drawbacks. For example, once the mapping files have been shipped with an SR Receiver system, the targeted SR Senders from which this SR Receiver can receive measurements are fixed. In order for this SR Receiver to receive measurements from a new SR Sender, new mapping files must be created and shipped to this SR Receiver's customers. In addition, any changes to DICOM measurement implementations by one of the targeted SR Senders such as, for example, the addition of more DICOM measurements or changing the encoding of existing DICOM measurements, will require engineers of this SR sender to inform the engineers of the SR Receiver to update the mapping file to reflect the changes and ship the updated mapping file to the SR Receiver customers. In reality, however, such communication between different manufacturers is time consuming for engineers of both the SR Receiver and the SR Sender. It may become difficult and error-prone for the SR Receivers to maintain different versions of multiple mapping files. Additionally, any measurements defined by SR Sender users cannot be transferred using a DICOM scheme or must be transferred in a limited DICOM scheme since the user-defined measurements will not will not be identified in the original mapping files.

A method for mapping standard measurements to local measurements. The method including reading a structured report information object, matching the standard measurements from the structured report information object to corresponding existing local measurements from a local measurement database and generating a summary page including the matched standard measurements and the corresponding existing local measurements and further including unmatched standard measurements that do not correspond to local measurements.

A system for mapping standard measurements to local measurements having a memory storing local measurements and corresponding standard measurements and a processor reading a structured report information object and matching the standard measurements from the structured report information object to corresponding existing local measurements from the memory, the processor further generating a summary page including the matched standard measurements and the corresponding existing local measurements and further including unmatched standard measurements that do not correspond to local measurements.

A computer-readable storage medium including a set of instructions executable by a processor. The set of instructions operable to read a structured report information object, match the standard measurements from the structured report information object to corresponding existing local measurements from a local measurement database and generate a summary page including the matched standard measurements and the corresponding existing local measurements and further including unmatched standard measurements that do not correspond to local measurements.

The exemplary embodiments may be further understood with reference to the following description and the appended drawings, wherein like elements are referred to with the same reference numerals. The exemplary embodiments relate to a system and method for providing a local measurement information model that facilitates transferability of the local measurement between medical devices and/or systems, even when the medical devices/systems are by different manufacturers. In particular, the exemplary embodiments describe a local measurement information model that includes DICOM measurement terms and designs, while maintaining local measurement terms, such that the local and DICOM measurements are interoperable and easily transferable. It will be understood by those of ordinary skill in the art that although the exemplary embodiments specifically describe DICOM measurements, terms and protocols, the exemplary embodiments may facilitate transferability of measurements using any accepted or known measurement standard.

Figure 1:
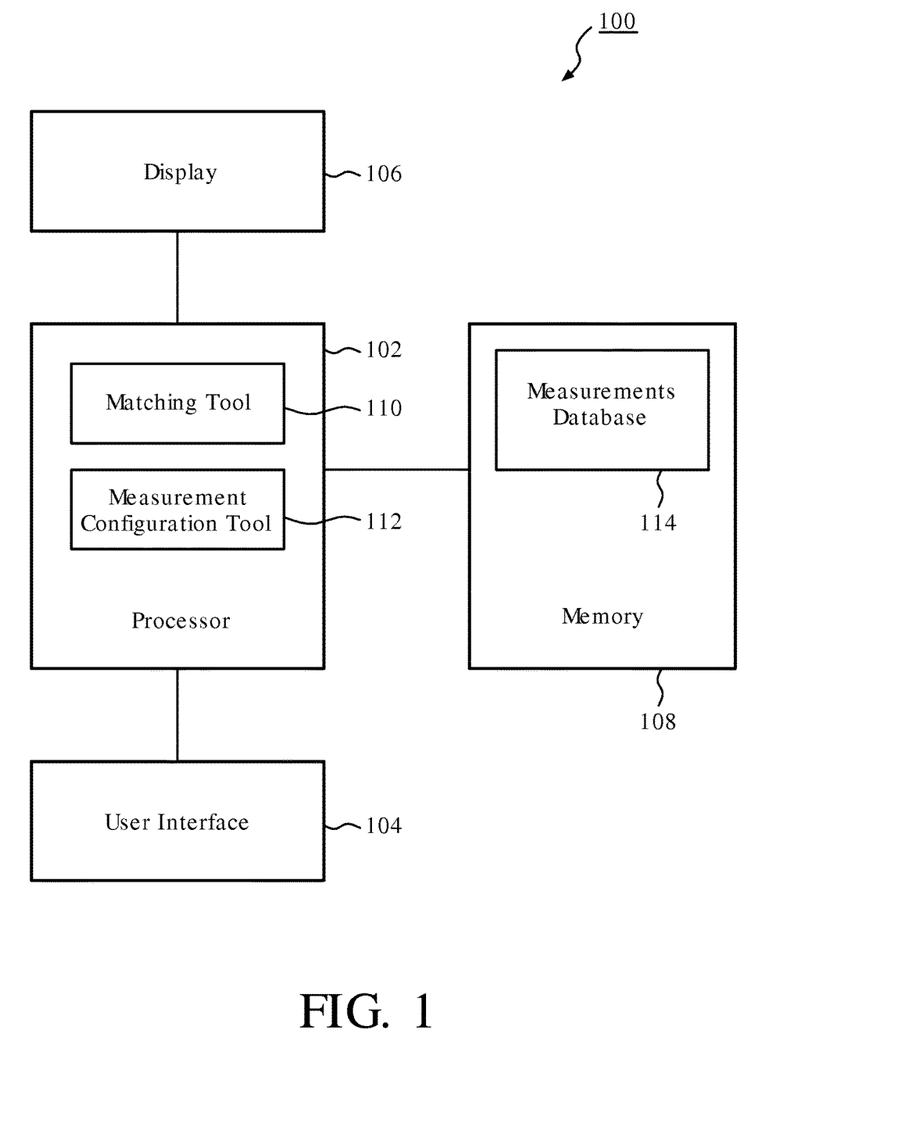
FIG. 1 shows a schematic diagram of a system according to an exemplary embodiment.

FIG. 1 shows a system 100 according to an exemplary embodiment. It is noted that in this embodiment, mapping files are not required to convert accepted standard measurements, such as DICOM measurements, to local measurements. System 100 comprises a processor 102, a user interface 104, a display 106 and a memory 108. The processor 102 executes a matching tool 110 embodied as a software application comprising a set of computer-readable instructions that, when executed, matches DICOM measurements to local measurements of a local device (i.e., SR Receiver and SR Sender), provided in step 220 of FIG. 2 and described further below. Local measurements are stored in a measurement database 114, which includes local measurement definitions and corresponding DICOM measurement definitions. The measurements database 114 is stored in the memory 108. It will be understood by those of skill in the art that the measurements database 114 is searchable via both a DICOM measurement definitions and a local measurement definitions.

Figure 4:
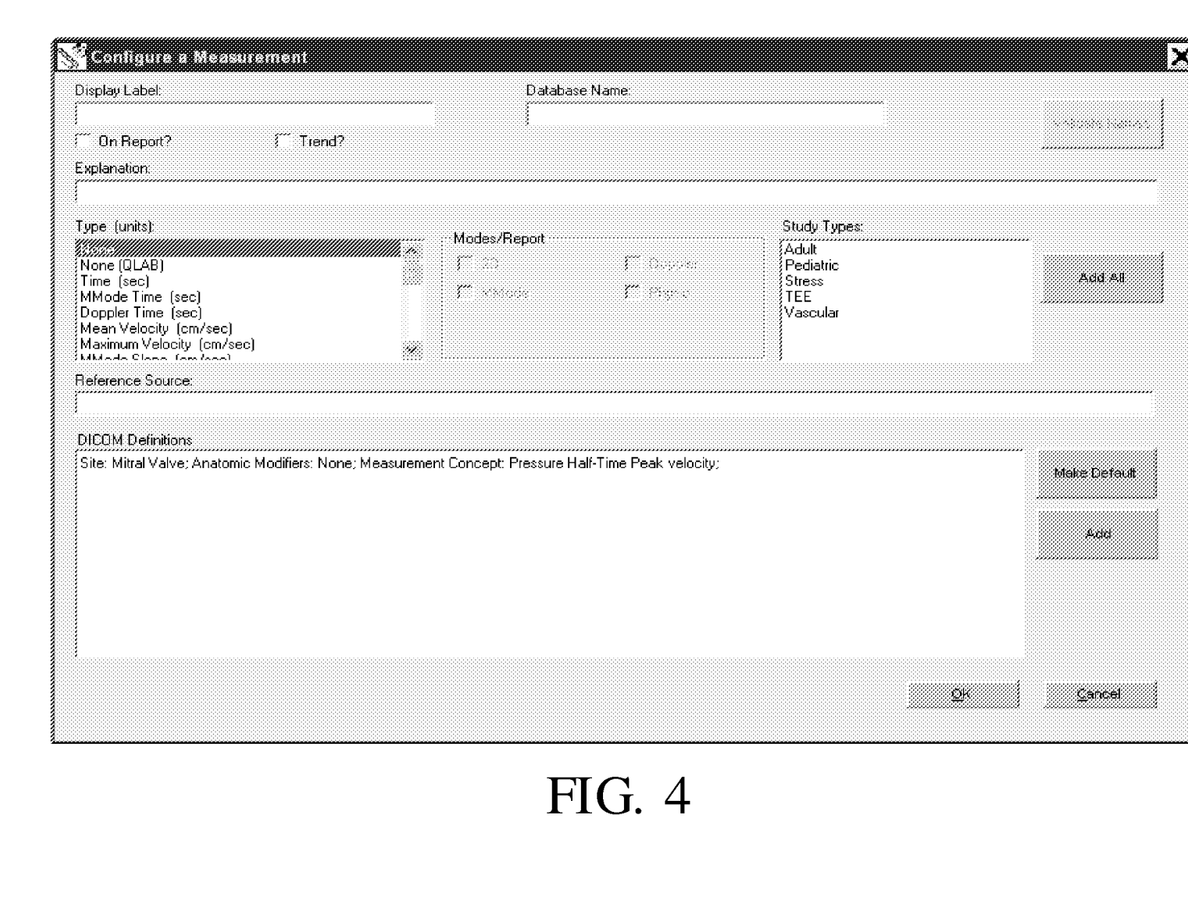
FIG. 4 shows a screen shot of an exemplary measurement configuration tool for matching an unknown DICOM measurement according to the method of FIG. 2.

The processor 102 also executes a measurement configuration tool 112 embodied as a software application comprising a GUI shown in FIG. 4 below and a set of computer-readable instructions that when executed permits an end-user to add new local measurements and/or edit existing local measurements in the measurements database 114. Additions and edits are inputted, for example, via the user interface 104. The user interface 104 includes, for example, a mouse or a touch screen display. It will be understood by those of skill in the art that the memory 108 is, for example, any known computer-readable medium, which is, for example, used for storage or other well-known purposes. It will also be understood by those of skill in the art that the system 100 is, for example, a personal computer or any other processing arrangement.

Figure 2:
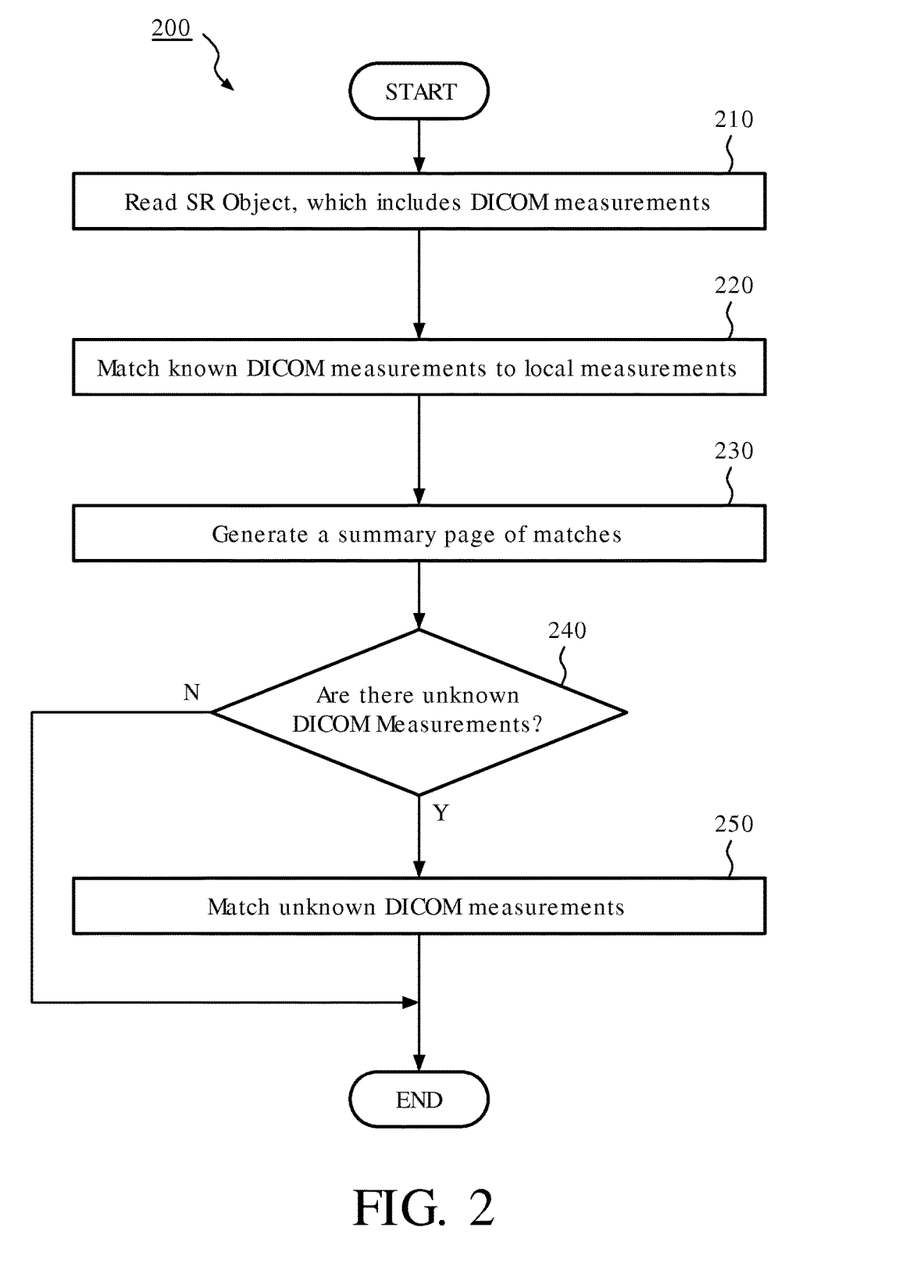
FIG. 2 shows a flow diagram of a method according to an exemplary embodiment.
Figure 3:
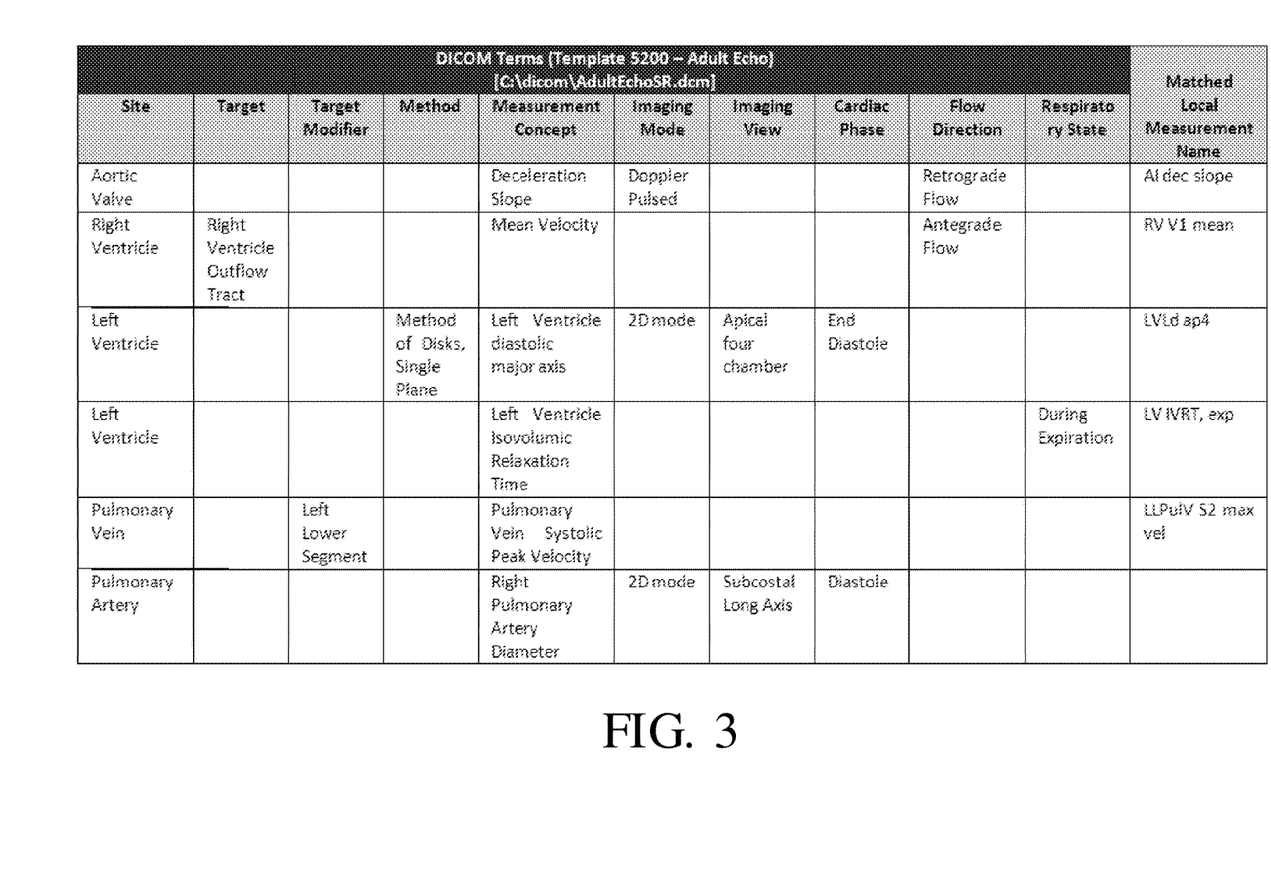
FIG. 3 shows a screen shot of an exemplary summary page of matches according to the method of FIG. 2.

As shown in FIG. 2, a method 200 according to an exemplary embodiment comprises reading an SR Object via, for example, the matching tool 110 of the system 100, in a step 210. Depending on whether the system 100 is an SR Sender or an SR Receiver, the SR Object file has been generated or received, respectively, by the system 100. The matching tool 110 reads the SR Object, matching all known DICOM measurements contained in the SR Object to corresponding existing local measurements in the measurement database, in a step 220. Based on the matched DICOM measurements, a summary page of matches is generated, in a step 230. As shown in FIG. 3, the summary page of matches is displayed as a table on the display 106, with a top row of the table representing DICOM codes, which are used to match the DICOM measurements to local measurements, and each of the subsequent rows of the table representing a DICOM measurement contained in the SR Object. The individual constituents of each row represent DICOM terms defining the DICOM measurement, each of the DICOM terms associated with a DICOM code in the top row. The column with the heading "Matched Local Measurement" shows the existing local measurements that have been matched to the DICOM measurements of the SR Object.

In a step 240, the method 200 determines whether any unknown DICOM measurements exist. An unknown DICOM measurement is one in which a corresponding local measurement cannot be determined. The unknown DICOM measurement may also be shown in the summary page of matches. Specifically, an unknown DICOM measurement is shown with a blank node at the bottom of the matched local measurement column of FIG. 3. Thus, the determination of whether an unknown DICOM measurement exists may also be made visually by the user by determining whether a blank node exists in the matched local measurement column of the summary page. It will also be understood by those of skill in the art that there may be a number of reasons for the unknown DICOM measurement. For example, the SR Sender that generated the SR Object may have changed its DICOM measurement implementations since the last time the matching tool 110 was used. Alternatively, the SR Sender that generated the SR Object may be a new SR Sender that has just been added to the SR Receiver's target list.

If it is determined in the step 240 that there are no unknown DICOM measurements, the method 200 ends. If, however, it is determined that there are unknown DICOM measurements, the unknown DICOM measurement is matched, in a step 250. The unknown DICOM measurement is matched in one of two ways. In a first way, the user elects to create a new local measurement. In a second way, the user may elect to match the unknown DICOM measurement to an existing local measurement. Matching of the unknown DICOM measurement is initiated by selecting the unknown DICOM measurement from the summary page. The unknown DICOM measurement is selected via the user interface by, for example, clicking on the unknown DICOM measurement row or by selecting the blank node in the "Matched Local Measurement" column using a mouse or a touch screen display. Selection of the unknown DICOM measurement launches the measurement configuration tool 112, as shown in FIG. 4. The configuration tool 112 includes a window showing list boxes, which are pre-filled with the DICOM terms associating the unknown DICOM measurement to the existing local measurement. Thus, the user either creates a new local measurement or selects an existing local measurement from the list boxes for the corresponding DICOM measurement. Once the unknown DICOM measurement is matched, it may be considered a newly known DICOM measurement. The newly known DICOM measurement and the corresponding local measurement may be saved to the memory 108 so that any future SR Objects including the newly known DICOM measurement may be matched as a known DICOM measurement.

For cases where the unknown DICOM measurement is matched to an existing local measurement, the user matches the unknown DICOM measurement to the existing local measurement regardless of whether the existing local measurement is already matched and corresponds to a known DICOM measurement. Thus, a single local measurement may be matched to multiple DICOM measurements. If there are multiple DICOM measurements for a single local measurement, the user selects a default DICOM definition to correspond to the local measurement. It will be understood by those of skill in the art that the steps 240-250 may be repeated until all of the unknown DICOM measurements of the SR Object have been matched.

Alternatively, the user may review the summary page generated in the step 230 to determine whether any edits are required for matched DICOM measurements. For example, where a known DICOM measurement requires an edit or change, the user selects the row or node of the DICOM measurement requiring an edit, which will allow the user to input additions/edits, as described below in regard to the method 300. It will be understood by those of skill in the art that where the system 100 is an SR Sender, unknown DICOM measurements will not exist since the SR Sender has generated the SR Object. All of the DICOM measurements will have matched corresponding local measurements, allowing the method 200 to skip steps 220, 240 and 250. In this case, the user may review the summary page of matches displayed in step 230 to determine whether any edits or changes are necessary.

Figure 5:
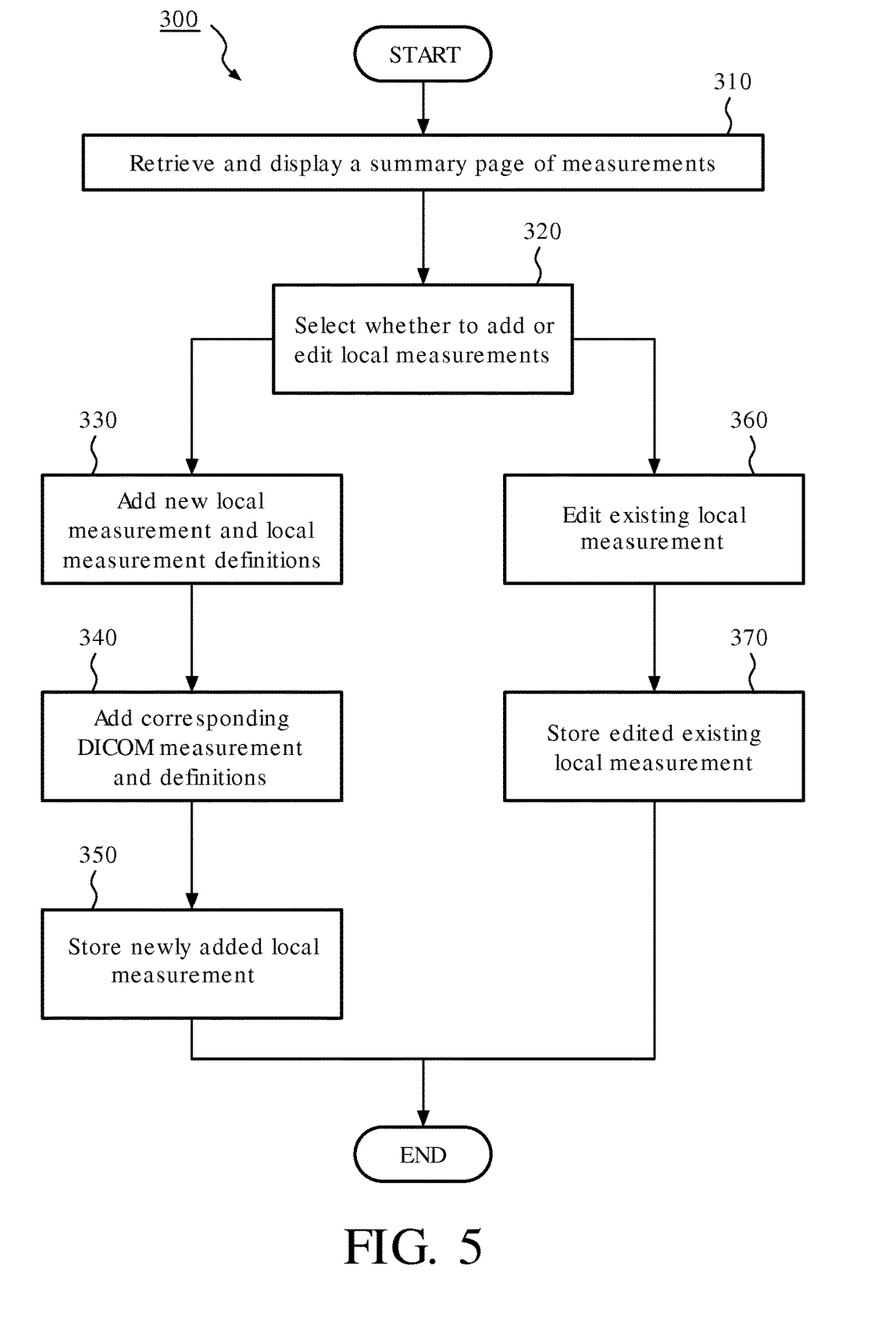
FIG. 5 shows a flow diagram of a method according to another exemplary embodiment.
Figure 6:
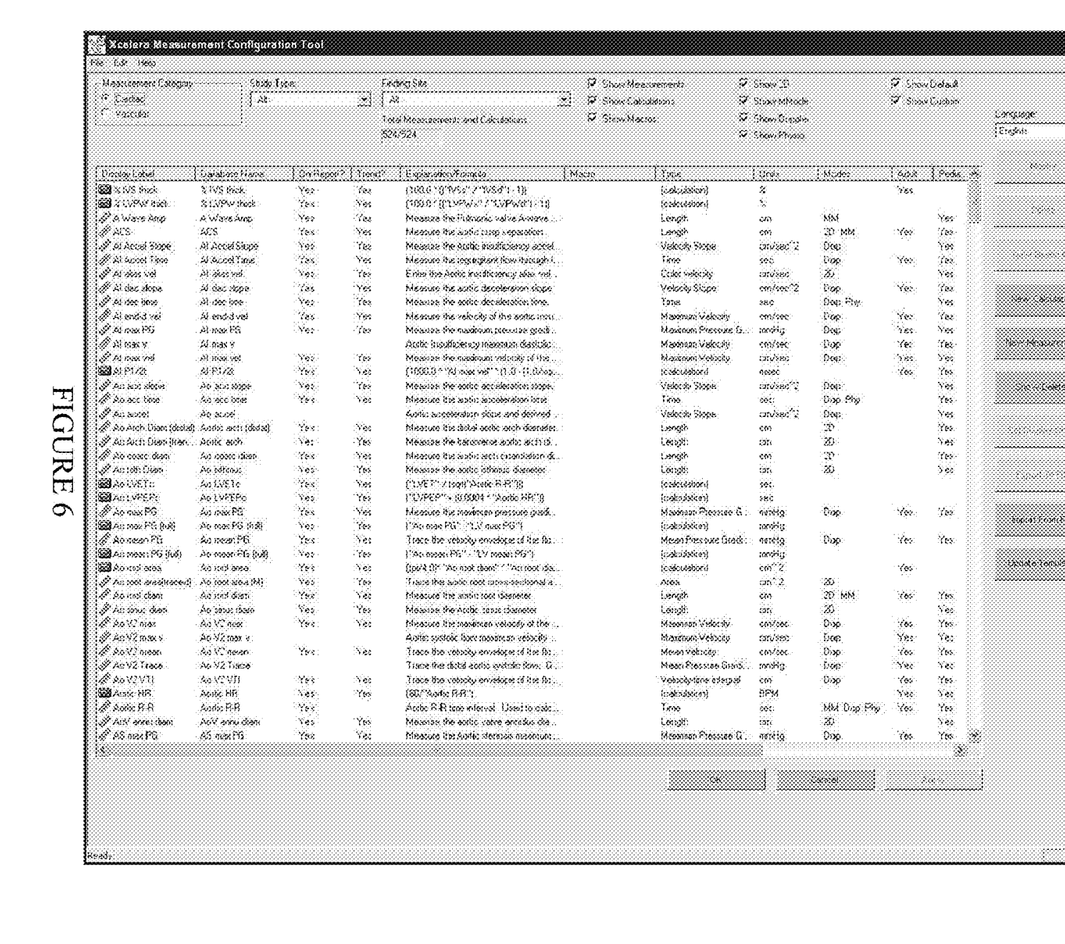
FIG. 6 shows a screen shot of an exemplary summary page of local measurements according to the method of FIG. 5.
Figure 7:
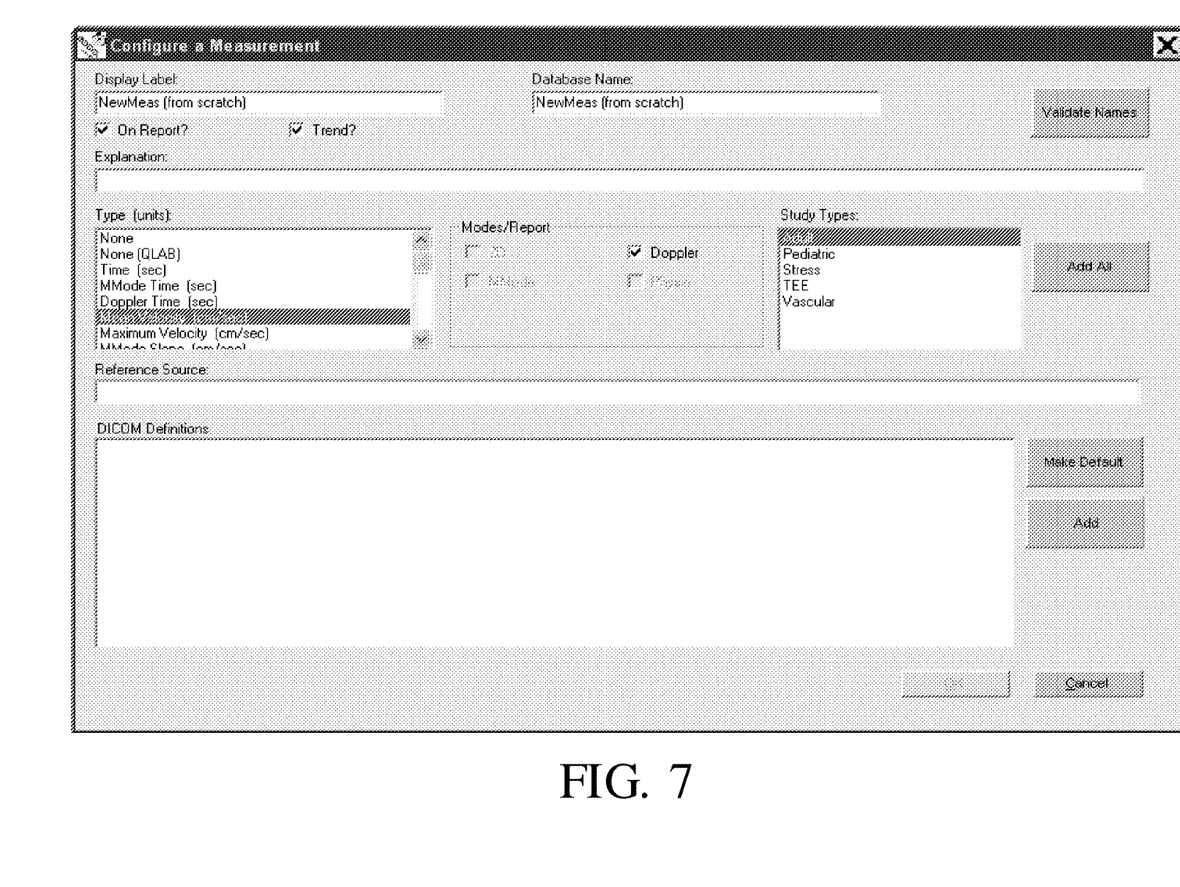
FIG. 7 shows a screen shot of an exemplary measurement configuration tool for adding a new local measurement according to the method of FIG. 5.

According to another exemplary embodiment, as shown in FIG. 5, a method 300 launches the measurement configuration tool 112 to add and/or edit local measurements. The method 300 comprises retrieving all locally defined measurements from the measurements database 114 and displaying a summary page of measurements, as shown in FIG. 6, on the display 106, in a step 310. In a step 320, the user selects one of two courses of action to take next. The user either selects to add a new local measurement or to edit an existing local measurement from the summary page. The user elects to add a new local measurement by selecting a new measurement option via the user interface 104. As shown in FIG. 7, selecting the new measurement option displays a window via which the user may input a new local measurement and terms defining the new local measurement, in a step 330. The dialog box includes list boxes in which the user inputs data or from which terms defining the local measurement are selected. For example, the list boxes include categories such as, Type (units), Mode, Study Type, Display Label, etc. However, it will be understood by those of skill in the art that any number of categories of list boxes may be included in the dialog box.

Figure 8:
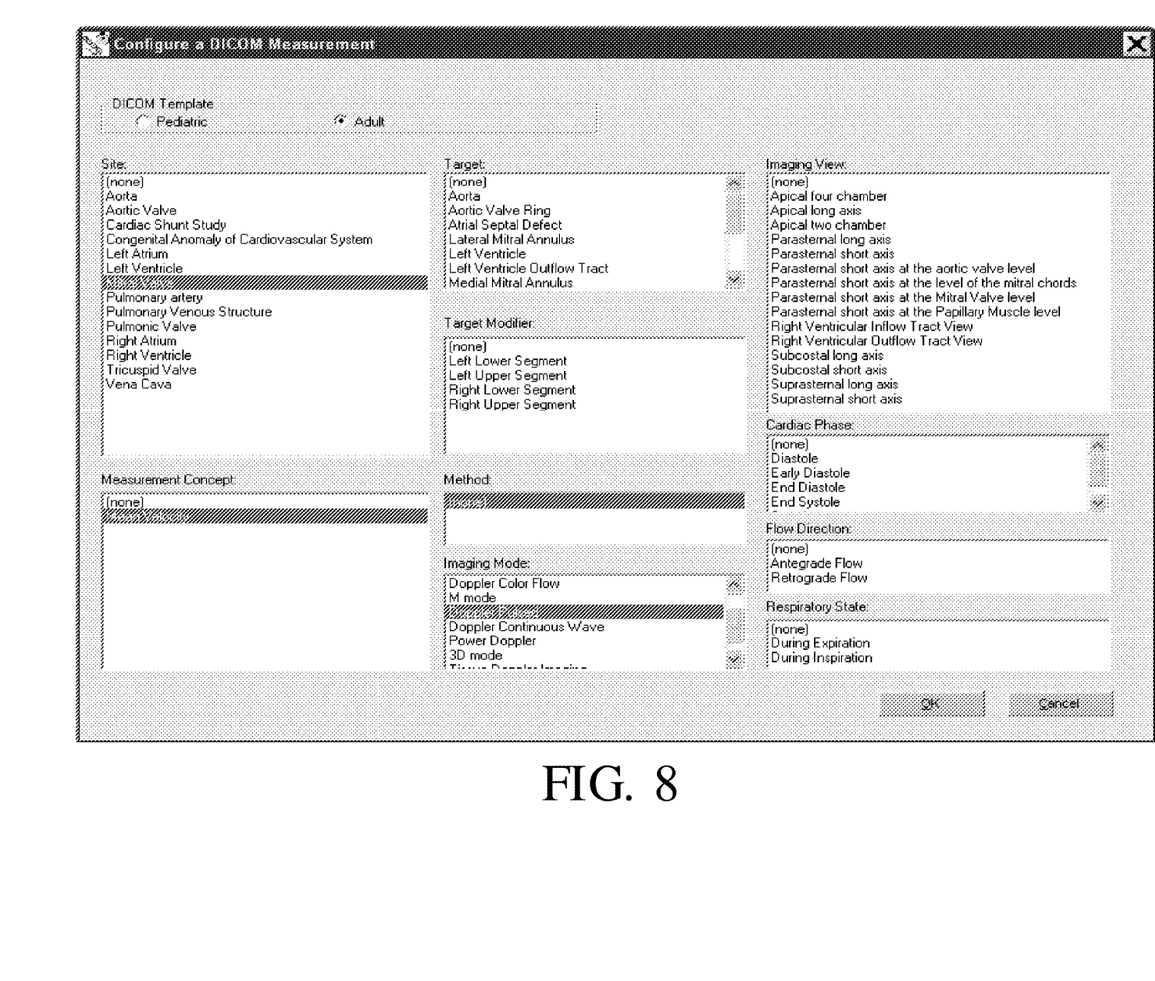
FIG. 8 shows a screen shot of an exemplary DICOM measurement configuration window for inputting DICOM measurement definitions of the new local measurement according to the method of FIG. 5.

Once the new local measurement and the new local measurement definitions have been inputted, a corresponding DICOM measurement and DICOM terms defining the DICOM measurement are also inputted, in a step 340. The corresponding DICOM measurement and terms may be added by selecting an add option on the dialog box, shown in FIG. 7, for inputting new local measurements, which is displayed in the step 330. Selecting the add option may display a window for DICOM measurements, as shown in FIG. 8. The window for DICOM measurements includes options for selecting a template and a set of list boxes along with various choices from each list box that the user may choose to define the DICOM measurement. For example, to define an adult echo measurement, the user specifies Site, Target, Target Modifier, Imaging View, Cardiac Phase, Flow Direction, etc., based upon the selected template. Once the corresponding DICOM measurement has been added, the new local measurement is stored in the memory 108, in a step 350, so that the mapping for the new local measurement to/from the corresponding DICOM measurement is available.

Figure 9:
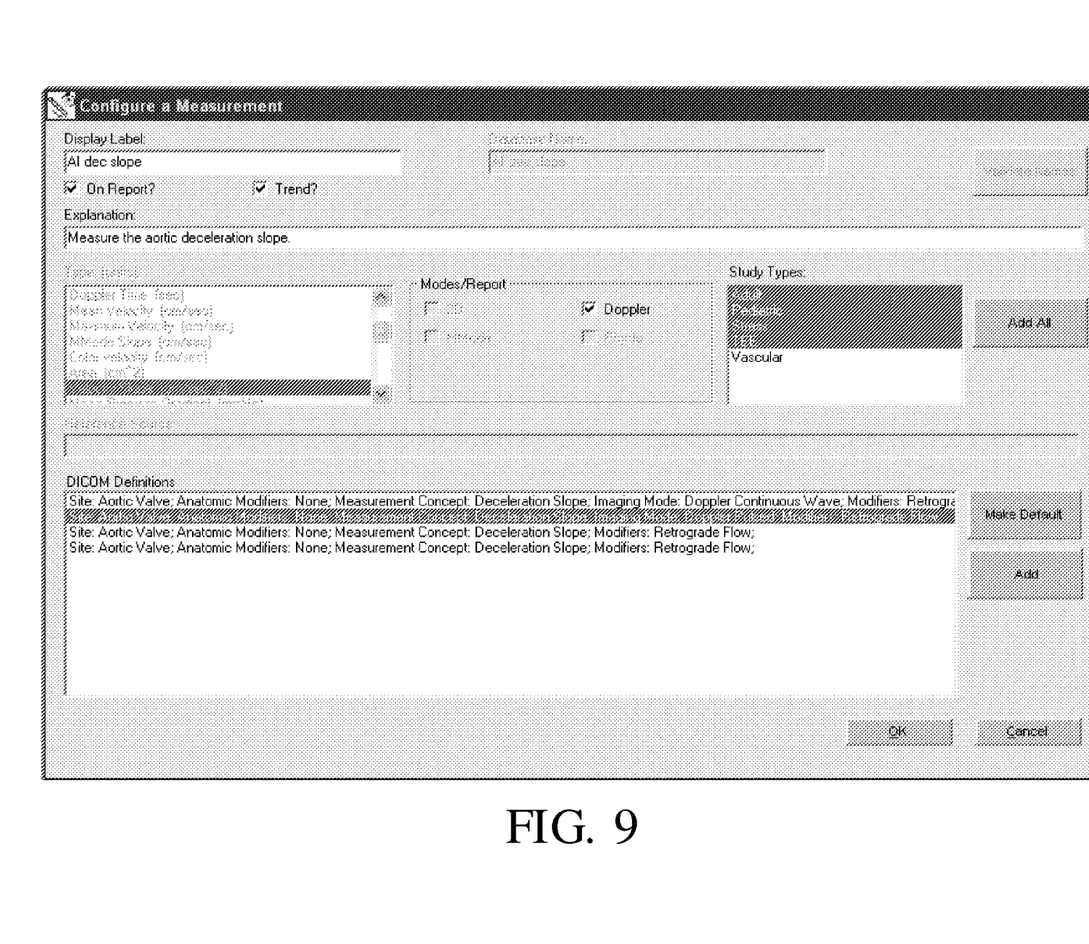
FIG. 9 shows a screen shot of the exemplary measurement configuration tool for editing an existing local measurement according to the method of FIG. 5.

Alternatively, the user may elect to edit an existing local measurement, in the step 320, by selecting one of the local measurements shown on the summary page, shown in FIG. 6, via the user interface 104. Selecting the existing local measurement displays a window via which the user inputs local measurement definitions, as shown in FIG. 9. The window is similar to the window of local measurements described in regard to the step 330 and shown in FIG. 7. However, the dialog box displayed when editing an existing local measurement will have all of the list boxes pre-filled with the existing local measurement definitions and the corresponding DICOM measurement definitions. For example, selecting the "A1 dec slope" measurement from FIG. 6 will display the dialog box of FIG. 9, with the list boxes pre-filled, as shown. To edit the existing local measurement terms defining the local measurement and/or the corresponding DICOM measurement terms, in a step 360, the user selects and/or inputs a different choice in the corresponding list box. Once the existing local measurement has been edited as desired, an update of the existing local measurement is stored, in a step 370, to the measurement database 114 so that the mapping for the local measurement to/from the DICOM measurement is also updated.

It will be understood by those of skill in the art that after the completion of either of the steps 350 or 370, the method 300 may return to the step 320 so that the user may continue to add/change local measurement definitions, as desired.

It will be apparent to those skilled in the art that various modifications may be made in the present disclosure, without departing from the spirit or the scope of the disclosure. Thus, it is intended that the present disclosure cover modifications and variations of this disclosure provided they come within the scope of the appended claims and their equivalents.

It is also noted that the claims may include reference signs/numerals in accordance with PCT Rule 6.2 (b). However, the present claims should not be considered to be limited to the exemplary embodiments corresponding to the reference signs/numerals.

The invention claimed is:

1. A method for mapping medically related standard measurements from a structured report information object to medically related local measurements, comprising:

storing, with a processor, existing medically related local measurements stored in a measurement database stored in a memory;

reading, with the processor, the structured report information object, wherein the structured report information object includes medical image data of a subject and the medical related standard measurements measure the medical image data from the medical scan of the subject;

matching, with the processor, the medically related standard measurements from the structured report information object to corresponding existing medically related local measurements from the measurement database;

storing, with the processor, the matched medically related local measurements and the corresponding medically related standard measurements in the measurement database stored in the memory; and generating, with the processor, a summary page including the matched medically related standard measurements and the corresponding existing medically related local measurements and further including unmatched medically related standard measurements that do not correspond to medically related local measurements.

2. The method of claim 1, further comprising:
   displaying the summary page.

3. The method of claim 2, wherein the medically related standard measurements are DICOM measurements based on a scan of a subject from a medical imaging device, the summary page is displayed as a table on a display, with a top row of the table representing DICOM codes, which match the DICOM measurements to the medically related local measurements, and each row of the table represents a DICOM measurement contained in the object, and individual constituents of each row represent DICOM terms defining the DICOM measurement, with each of the DICOM terms associated with a DICOM code in the top row, and a matched local measurement column shows the existing medically related local measurements that are matched to the DICOM measurements of the object, wherein an unknown DICOM measurement is shown with a blank node at the bottom of the matched local measurement column.

4. The method of claim 1, further comprising:
   matching the unmatched medically related standard measurements.

5. The method of claim 4, wherein matching the unmatched medically related standard measurements includes creating a new medically related local measurement, the new medically related local measurement including a corresponding medically related standard measurement information.

6. The method of claim 4, wherein matching the unmatched medically related standard measurements includes selecting an existing medically related local measurement from the local measurement database.

7. The method of claim 4, further comprising:
selecting a default medically related local measurement to correspond to the unmatched medical related standard measurements.

8. The method of claim 4, further comprising:
storing the matching of the unmatched medically related standard measurements in the measurement database.

9. A system for mapping medically related standard measurements to medically related local measurements, comprising:
a memory storing medically related local measurements and corresponding medically related standard measurements; and
a processor reading a structured report information object, matching the medically related standard measurements from the structured report information object to corresponding existing medically related local measurements from the memory, and storing the matched medically related local measurements and the corresponding medically related standard measurements in the measurement database stored in the memory, and the processor further generating a summary page including the matched medically related standard measurements and the corresponding existing medically related local measurements and further including unmatched medically related standard measurements that do not correspond to medically related local measurements, wherein the structured report information object includes medical image data of a subject measured by the medically related standard measurements from the structured report information object; a medical imaging system that packages the medically related standard measurements and the medical image data in the structured report information object, wherein the medical image data is generated from a scan of a patient by at least one imaging modality selected from a group comprising of computed tomography (CT), magnetic resonance (MR), and X-ray.

10. The system of claim 9, further comprising:
a display displaying the summary page.

11. The system of claim 10, wherein the memory stores the medically related local measurements and the corresponding medically related standard measurements in a measurement database.

12. The system of claim 9, wherein the processor matches the unmatched medically related standard measurements.

13. The system of claim 12, further comprising:
a user interface, wherein matching the unmatched medically related standard measurements includes creating a new medically related local measurement via the user interface, the new medically related local measurement including a corresponding medically related standard measurement information.

14. The system of claim 12, further comprising:
a user interface, wherein matching the unmatched medically related standard measurements includes selecting an existing medically related local measurement from the memory via the user interface.

15. The system of claim 12, further comprising:
a user interface for selecting a default medically related local measurements to correspond to unmatched medically related standard measurements.

16. The system of claim 9, further comprising:
a user interface for inputting one of a medically related local measurement information and a DICOM measurement information.

17. The system of claim 9, wherein the medically related standard measurements are DICOM measurements.

18. A non-transitory computer-readable storage medium including a set of instructions executed by a processor, the set of instructions operable to:
store existing medically related local measurements in a local measurement database stored in a memory;
read a structured report information object, wherein the structured report information object includes medical image data of a subject and medical related standard measurements that measure the medical image data of the subject; wherein the medical image data of the subject is generated by a medical imaging that includes at least one modality selected from a group comprising of computed tomography (CT), magnetic resonance (MR), and X-ray;
match the medically related standard measurements from the structured report information object to corresponding existing medically related local measurements from the local measurement database;
store the matched medically related local measurements and the corresponding medically related standard measurements in the measurement database stored in the memory; and
generate a summary page including the matched medically related standard measurements and the corresponding existing medically related local measurements and further including unmatched medically related standard measurements that do not correspond to medically related local measurements.

* * * * *